(12) United States Patent
Salahshoor Kordestani (10) Patent No.: US 10,589,029 B2
(45) Date of Patent: Mar. 17, 2020

(54) ADJUSTABLE NEEDLE-FREE INJECTOR

(71) Applicant: ChitoTech (Keifiat Tolid Takapoo), Tehran (IR)

(72) Inventor: Soheila Salahshoor Kordestani, Tehran (IR)

(*) Notice: Subject to any disclaimer, the term of this patent is extended or adjusted under 35 U.S.C. 154(b) by 134 days.

(21) Appl. No.: 15/854,824

(22) Filed: Dec. 27, 2017

(65) Prior Publication Data

US 2018/0117253 A1    May 3, 2018

Related U.S. Application Data

(60) Provisional application No. 62/439,915, filed on Dec. 29, 2016.

(51) Int. Cl.
| | |
|---|---|
| *A61M 5/30* | (2006.01) |
| *A61M 5/24* | (2006.01) |
| *A61M 5/20* | (2006.01) |
| *A61M 5/315* | (2006.01) |

(52) U.S. Cl.
CPC ............ *A61M 5/30* (2013.01); *A61M 5/2033* (2013.01); *A61M 5/2422* (2013.01); *A61M 5/3158* (2013.01); *A61M 2005/2013* (2013.01); *A61M 2205/50* (2013.01); *A61M 2205/502* (2013.01); *A61M 2205/52* (2013.01)

(58) Field of Classification Search
CPC .... A61M 5/30; A61M 5/3007; A61M 5/3015; A61M 2005/3022; A61M 5/145; A61M 5/1454; A61M 5/14546; A61M 5/1456; A61M 5/2033; A61M 5/31526; A61M 5/3156; A61M 5/31563; A61M 2005/14506; A61M 5/202
See application file for complete search history.

(56) References Cited

U.S. PATENT DOCUMENTS

| | | | | |
|---|---|---|---|---|
| 2008/0243087 | A1* | 10/2008 | Enggaard | A61M 5/31553 604/208 |
| 2011/0319860 | A1* | 12/2011 | Williamson | A61J 1/2096 604/500 |
| 2014/0180210 | A1* | 6/2014 | Niklaus | A61M 5/14216 604/152 |
| 2016/0129188 | A1* | 5/2016 | Kiilerich | F16F 1/046 604/208 |
| 2017/0368261 | A1* | 12/2017 | Zhang | A61M 5/30 |
| 2018/0015221 | A1* | 1/2018 | Fujii | A61M 5/14546 |
| 2018/0036486 | A1* | 2/2018 | Yamamoto | A61M 5/315 |
| 2018/0272068 | A1* | 9/2018 | Ko | A61M 5/24 |

* cited by examiner

*Primary Examiner* — Rebecca E Eisenberg
*Assistant Examiner* — Dung T Ulsh
(74) *Attorney, Agent, or Firm* — Bajwa IP Law Firm; Haris Zaheer Bajwa (57) ABSTRACT

An adjustable needleless injection system for subcutaneous injection of a liquid medication to a patient is disclosed. The adjustable needleless injection system may include: a medication cartridge that holds the liquid medication, where the medication cartridge includes a cartridge piston, a spring-actuated injector that may be coupled with the medication cartridge and configured to selectively apply force to the cartridge piston, and a charging mechanism configured to charge the spring-actuated injector based on a body type of the patient.

9 Claims, 6 Drawing Sheets

ADJUSTABLE NEEDLE-FREE INJECTOR

CROSS-REFERENCE TO RELATED APPLICATION

This application claims the benefit of priority from pending U.S. Provisional Patent Application Ser. No. 62/439,915, filed on Dec. 29, 2017, and entitled "ADJUSTABLE PLC-BASED NEEDLE-FREE INJECTOR," which is incorporated herein by reference in its entirety.

TECHNICAL FIELD

The present disclosure relates to medicinal injecting systems, particularly to needle-free injection systems, and more particularly to an adjustable needle-free injection apparatus.

BACKGROUND

Needle injection is an invasive method of drug administration, which can cause tissue damage. Also, needle injections may be a source of disease transmission, particularly when needles are reused or misused.

Needle-free injection technologies have gained attention as a means for overcoming the numerous disadvantages of needle injections. Such needle-free injection technologies apply a high pressure to a medicinal fluid to force the fluid out of a small orifice held against a patient's skin. The pressurized medicinal fluid penetrates the skin and enters the tissue under the skin where it is absorbed. Needle-free injection technologies may be used for injecting liquid formulations, as well as drugs and vaccines in a solid particle dosage form. A needle-free injection may prevent skin puncture hazards, bleeding, and bruises. Needle-free injections may ensure a faster drug delivery and better reproducibility and bioavailability in comparison with invasive drug delivery systems.

Some needle-free injection systems use a high-pressure gas such as $CO_2$ for applying the required pressure to the medicinal fluid. Other needle-free injection systems use springs to force the medicinal fluid out of the injection system. These needle-free injection systems apply a fixed amount of force to subcutaneously inject the medicinal fluids to a patient. The amount of force required for a successful subcutaneous injection of the medicine is different for each body type, for example, the amount of force required for an adult is different from that required for a child. As a result, separate needle-free injection systems have been conventionally used for adults and children.

There is, therefore, a need in the art for a needle-free injection system that may be utilized for needle-free injections to different body types. There is further a need in the art for a needle-free injector that allows a user to select the amount of force applied to the medicine based on the patient's body type.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings of exemplary embodiments.

According to one or more exemplary embodiments, the present disclosure is directed to an adjustable needleless injection system for subcutaneous injection of a liquid medication to a patient. The disclosed system may include a medication cartridge that may be configured to hold the liquid medication, where the medication cartridge may include a cartridge piston. The system may further include a spring-actuated injector that may be coupled with the medication cartridge and may be configured to selectively apply injection force to the cartridge piston. The spring-actuated injector may include a spring-loaded injector piston with ratchets formed in a symmetrical arrangement along a portion of the injector piston, where the injector piston may include an injector spring positioned to apply the injection force to the injector piston. The spring-actuated injector may further include a spring-loaded trigger engaged with the ratchets on the injector piston to hold the injector piston in place against the injection force applied by the injector spring, where the trigger may be configured to selectively release the injector piston responsive to the trigger being pushed down, and the injector piston may be configured to release to move responsive to the injection force applied by the injector spring. The injector piston may be configured to apply the injection force to the cartridge piston to force the liquid medication out of the medication cartridge. The disclosed system may further include a charging mechanism that may be configured to charge the spring-actuated injector by applying a charging force to the injector piston to move the injector piston against the injection force of the injector spring by a predetermined distance. The charging mechanism may include a linear actuator configured to engage the injector piston, the linear actuator applying the charging force to the injector piston to move the injector piston against the injection force of the injector spring by the predetermined distance; a user interface unit configured to receive a body type from a user; a processor coupled with the charging mechanism; and a memory coupled to the user interface unit and the controller, the memory storing executable instructions to cause the processor to: receive the body type from the user interface unit; correlate the received body type with a required injection force; calculate the predetermined distance based on the required injection force; and cause the linear actuator to move the injector piston against the injection force of the injector spring by the predetermined distance.

According to some exemplary embodiments, the ratchets on the injector piston may be spaced apart by equal distances. Each ratchet corresponds to an incremental injecting force being applied by the injector spring to the injector piston. According to one exemplary embodiment, the ratchets on the injector piston may be spaced apart by at least 2 mm.

According to some exemplary embodiments, the user interface unit may be configured to receive the body type from the user as parameters selected from the group consisting of body mass index, age, gender, and anatomical site of injection.

According to one exemplary embodiment, the injector spring may have a spring constant between 2 N/mm and 7 N/mm. According to one exemplary embodiment, the predetermined distance may be calculated by Hooke's Law.

According to one or more exemplary embodiments, the present disclosure is directed to a method for charging a needle-free injector based on a body type of a patient receiving an injection. The method may include associating a spring-actuated needle-free injector with a charging mechanism, the spring actuated needle-free injector including an injector piston actuated by an injector spring and a trigger mechanism configured to hold the injector piston in place against the injecting or injection force applied by the injector spring; the charging mechanism including a linear actuator engaging the injector piston, the linear actuator applying charging force to the injector piston to move the injector piston against the injection force of the injector spring by a predetermined distance, receiving the body type, correlating the received body type with a required injection force, calculating the predetermined distance based on the required injection force, and moving the injector piston against the injection force of the injector spring by the predetermined distance using the linear actuator.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

In a needle-free injection system, a medicine is injected through the skin of a patient. The injected medicine must reach the underlying tissues in order to be absorbed. Therefore the amount of injection force exerted by the needle-free injection system must be carefully adjusted to ensure a successful subcutaneous injection of the medicine. The amount of injection force required to inject the medicine through the skin may vary depending on the type of the patient's body. For example, the amount of injection force required for a successful subcutaneous injection for an adult is different from the injection force required for a child. In another example, the amount of injection force required for a successful subcutaneous injection for an average adult is different from the injection force required for a heavy-weight adult. Most needle-free injection systems have been designed separately for adults and children. In other words, one injection system must be used for adults and another injection system must be used for children.

Disclosed exemplary needle-free injection systems and devices include a needle-free injector and a smart charging mechanism. The smart charging mechanism allows a user to adjust the amount of injection force exerted by the needle-free injector based on the type of the patient's body. This feature allows the user to use a single needle-free injector for children, average-weight adults, heavy-weight adults, or any other patient with a certain body type. The needle-free injector may be a spring-actuated injector including a spring and the smart charging mechanism may be configured to charge the injector by compressing the spring to a certain extent based on the type of the body selected by the user.

Figure 1:
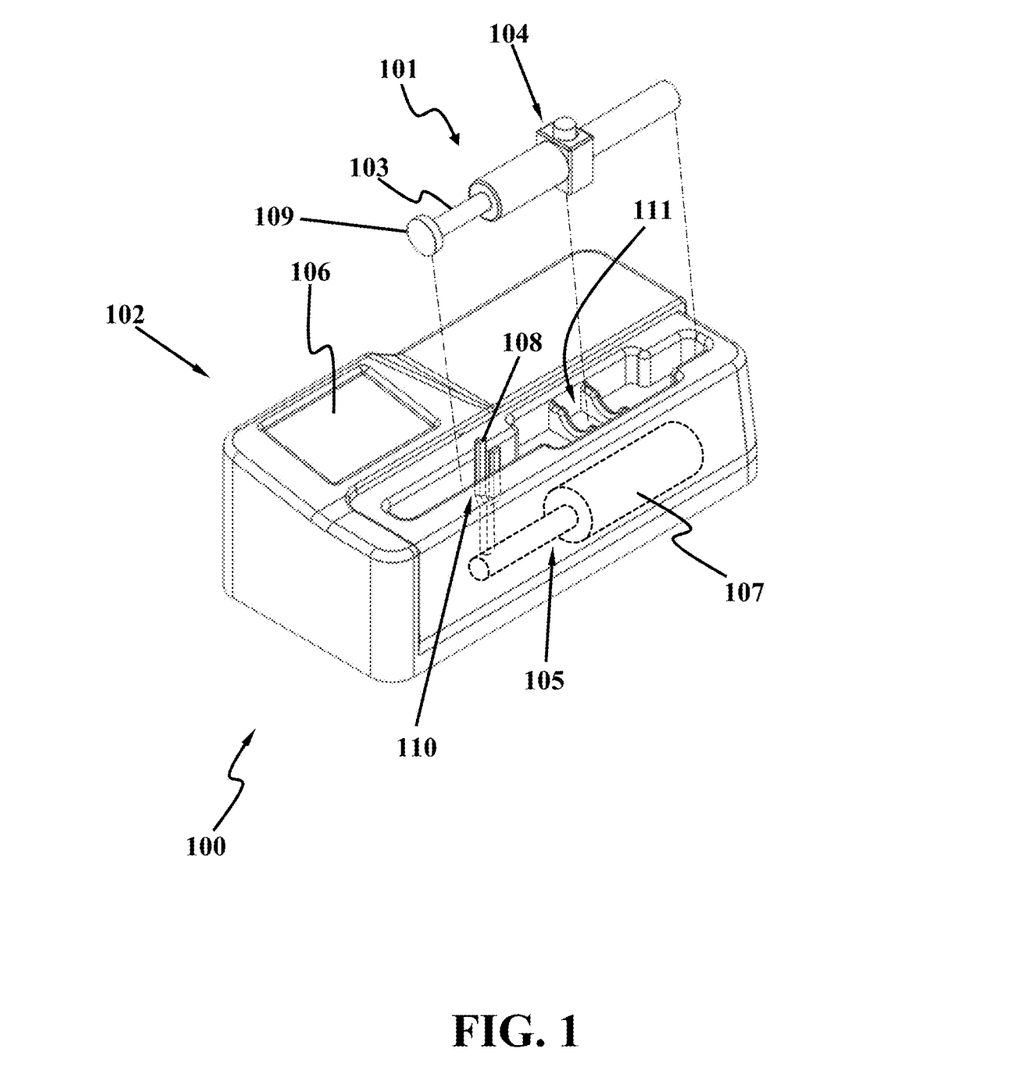
FIG. 1 illustrates a perspective view of a needle-free injection device, consistent with one or more exemplary embodiments of the present disclosure.

FIG. 1 illustrates a perspective view of a needle-free injection device 100, consistent with one or more exemplary embodiments of the present disclosure. The needle-free injection device 100 may include a needle-free injector 101 and a smart charging assembly 102. Needle-free injector 101 may include an injector piston 103 and a trigger mechanism 104. Injector piston 103 may be a spring-loaded piston that may be held in place against the injection force of a spring by trigger mechanism 104. Smart charging assembly 102 may include a charging mechanism 105 and a user interface unit 106. Needle-free injector 101 may be receivable in the charging mechanism 105. Charging mechanism 105 may include a linear actuating mechanism 107 coupled with an engagement member 108. Engagement member 108 may be configured to engage injector piston 103 once needle-free injector 101 is received in the charging mechanism 105.

Figure 2A:
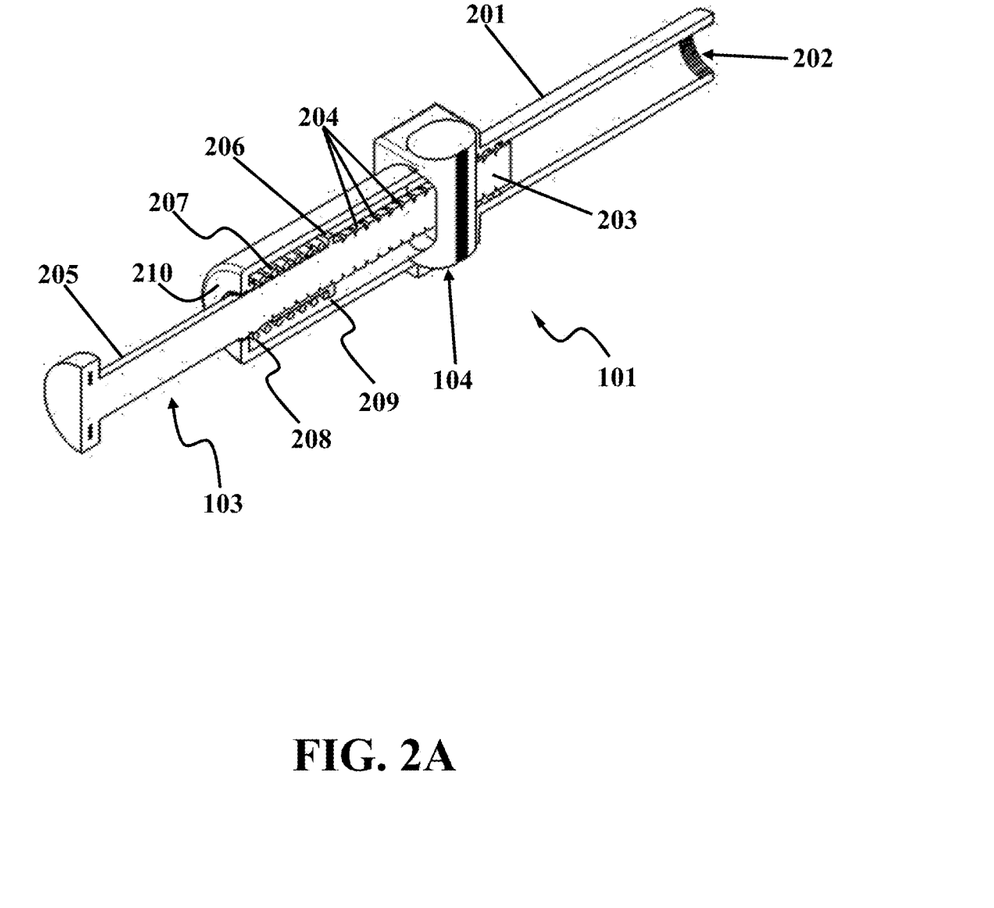
FIG. 2A illustrates a sectional perspective view of a needle-free injector, consistent with one or more exemplary embodiments of the present disclosure.
Figure 2B:
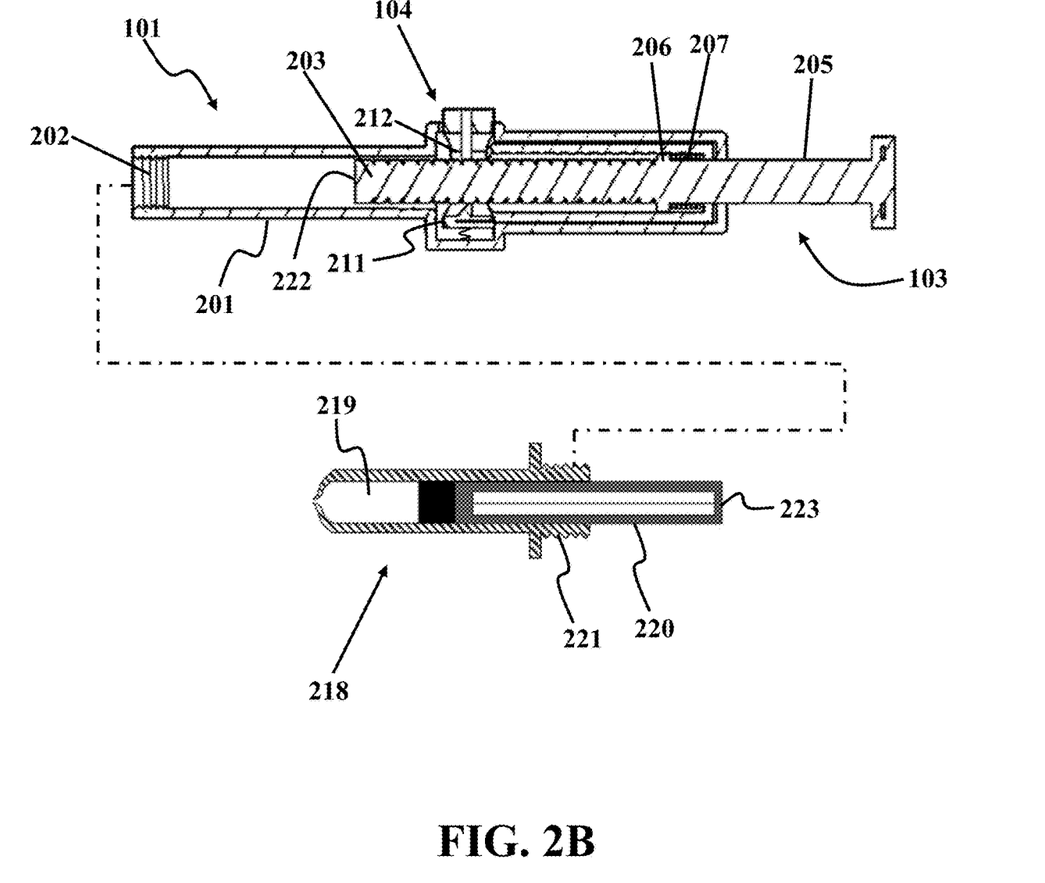
FIG. 2B illustrates a sectional view of a needle-free injector coupled with a medication cartridge assembly, consistent with one or more exemplary embodiments of the present disclosure.

FIG. 2A illustrates a sectional perspective view of needle-free injector 101, consistent with one or more exemplary embodiments of the present disclosure. FIG. 2B illustrates a sectional view of needle-free injector 101 coupled with a medication cartridge assembly 218, consistent with one or more exemplary embodiments of the present disclosure. Referring to FIGS. 2A and 2B, in an exemplary embodiment, needle-free injector 101 may further include a main body 201 that may house injector piston 103 and trigger mechanism 104. Main body 201 may further include a threaded portion 202 at a distal end of main body 201 that may function as a coupling means for coupling main body 201 with medication cartridge assembly 218. In an embodiment, a first portion 203 of injector piston 103 may be in the form of a ratchet rod with ratchets 204 formed along first portion 203. A second portion 205 of injector piston 103 may be a rod that is separated from first portion 203 by an extended retainer 206. A spring 207 that has a first end 208 and a second end 209 may be disposed around second portion 205 behind extended retainer 206, such that first end 208 is positioned against an inner surface of an inner proximal end 210 of main body 201 and second end 209 is positioned against extended retainer 206 of injector piston 103. Once injector piston 103 is pulled out along the longitudinal axis of injector piston 103, extended retainer 206 may apply force to second end 209 of spring 207 and thereby compress spring 207. As used herein, charging needle-free injector 101 refers to spring 207 being compressed to a certain extent. According to an exemplary embodiment, spring 207 may have a spring constant between 2 N/mm and 7 N/mm.

Figure 2C:
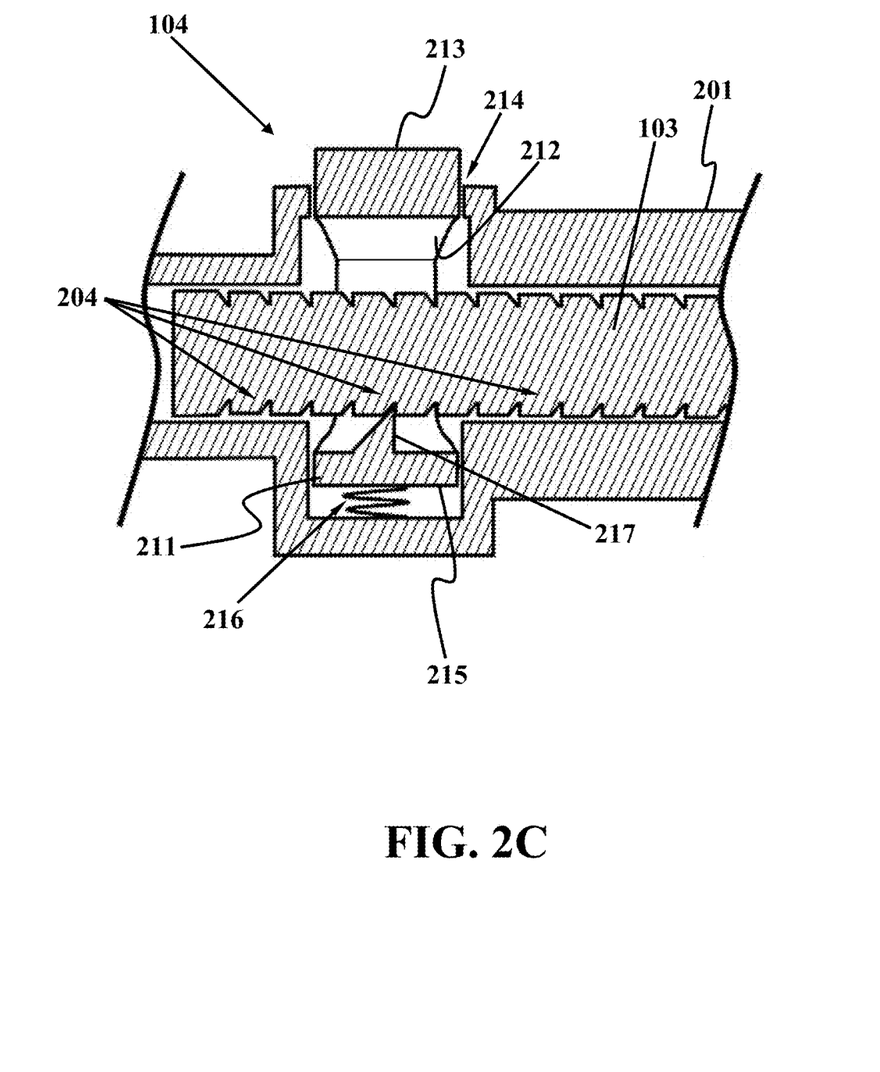
FIG. 2C illustrates a sectional view of a trigger mechanism, consistent with one or more exemplary embodiments of the present disclosure.

FIG. 2C illustrates a sectional view of trigger mechanism 104, consistent with an exemplary embodiment of the present disclosure. Referring to FIGS. 2A-2C, trigger mechanism 104 may include a spring-loaded trigger 211 with a side hole 212 formed through trigger 211. Side hole 212 may be sized to allow injector piston 103 to move back and forth through side hole 212. Spring-loaded trigger 211 may have a first end 213 extending out of a hole 214 in main body 201, first end 213 configured to function as a push button and a second end 215 that may rest upon a trigger spring 216. A finger 217 may be formed inside side hole 212 which may extend out of the inner surface of side hole 212 in the middle of spring-loaded trigger 211. Finger 217 may engage ratchets 204 on first portion 203 of injector piston 103. The finger 217 functions as a pawl in a ratchet mechanism only allowing movement in one direction. As injector piston 103 moves backward toward proximal end 210 of main body 201, the finger 217 follows the movement, but when injector piston 103 is forced to move forward by spring 207, spring-loaded finger 217 prevents forward motion and holds injector piston 103 in place against the injection force of spring 207.

Referring to FIGS. 2A-2C, in an exemplary embodiment, spring-loaded trigger 211 may be configured to selectively release injector piston 103 in response to first end 213 of spring-loaded trigger 211 being pushed down. Pushing spring-loaded trigger 211 down may force finger 217 down against the restoring force of trigger spring 216 and as a result, finger 217 is disengaged from ratchets 204 and injector piston 103 may be released to move in response to the injection force that is being applied by spring 207.

With further reference to FIG. 2B, cartridge assembly 218 may include a vial section 219 that may hold the liquid medication and a cartridge piston 220 that may move to force the liquid medication out of vial section 219. In an embodiment, cartridge assembly 218 may further include a threaded section 221 at a proximal end of cartridge assembly 218. Threaded section 221 may be used to couple cartridge assembly 218 to the distal end of needle-free injector 101, such that a distal end 222 of injector piston 103 may be positioned near a proximal end 223 of cartridge piston 220. In an exemplary embodiment, once needle-free injector 101 is charged, i.e., spring 207 is compressed to a certain extent, pushing spring-loaded trigger 211 down may force finger 217 down against the restoring force of trigger spring 216 and as a result finger 217 may be disengaged from ratchets 204 and injector piston 103 may be released to move in response to the injection force that is being applied by spring 207. Injector piston 103 may then move to exert a force on cartridge piston 220 and force cartridge piston 220 forward and thereby force the liquid medication out of medication cartridge 218. The injection force exerted by injector piston 103 to cartridge piston 220 may be proportional to the injection force exerted by spring 207 to injector piston 103. The injection force exerted by spring 207 on injector piston 103 may depend on a large part to the amount that spring 207 is charged, i.e., compressed. In one or more exemplary embodiments of the present disclosure, by changing the extent of spring 207 compression, difference forces may be applied to cartridge piston 220 and cartridge piston 220 may force the liquid medication out of medication cartridge 218 by different extents based on a body type of the patient.

Figure 3:
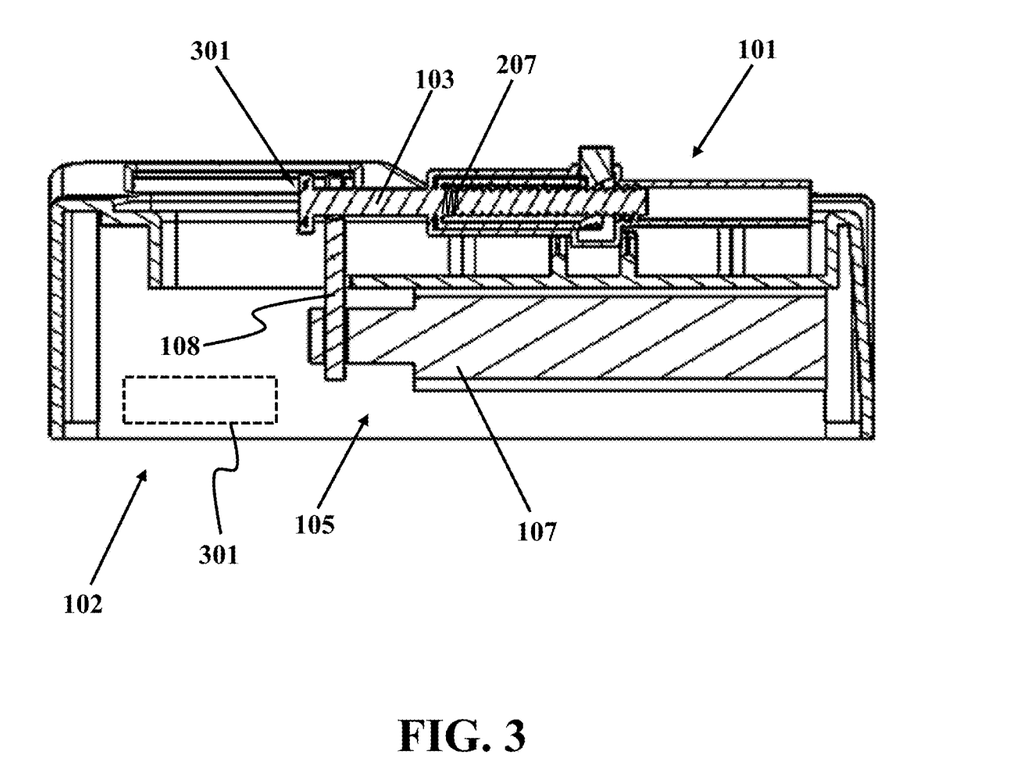
FIG. 3 illustrates a sectional view of a needle-free injector received inside a smart charging assembly, consistent with one or more exemplary embodiments of the present disclosure.

FIG. 3 illustrates a sectional view of needle-free injector 101 received inside smart charging assembly 102, consistent with one or more exemplary embodiments of the present disclosure. With reference to FIGS. 1 and 3, as mentioned before, in an exemplary embodiment, smart charging assembly 102 may include charging mechanism 105 and user interface unit 106. Charging mechanism 105 may include linear actuating mechanism 107 coupled with engagement member 108. In an exemplary embodiment, injector piston 103 may further include a radially extended section 109 at a distal end of injector piston 103. Engagement member 108 may have a U-shaped or a V-shaped distal end 110 which may be shaped to engage radially extended section 109. Linear actuating mechanism 107 may be a mechanism that transforms a rotary motion of an electric motor to a linear motion of engagement member 108. One needle-free injector 101 may be placed and secured in a housing 111 on smart charging assembly 102, U-shaped or V-shaped distal end 110 of engagement member 108 engages radially extended section 109 of injector piston 103, and linear actuating mechanism 107 may actuate injector piston 103 via engagement member 108 against the injection force of spring 207 and as a result, needle-free injector 101 may be charged. Smart charging assembly 102 may further include a controller 301 that may be coupled to charging mechanism 105 and user interface unit 106. User interface unit 106 may be configured to receive data input from a user. An exemplary embodiment of user interface unit 106 may include, for example, a graphical user interface (GUI) unit. User interface unit 106, in combination with controller 301, may allow the user to control the charging process of needle-free injector 101. Data input by the user may include, for example, body mass index, anatomical site of injection, age, and gender. Controller 301 may be configured to adjust the depth of medication penetration by urging charging mechanism 105 to charge needle-free injector 101 to an extent corresponding to the data input by the user.

Figure 4:
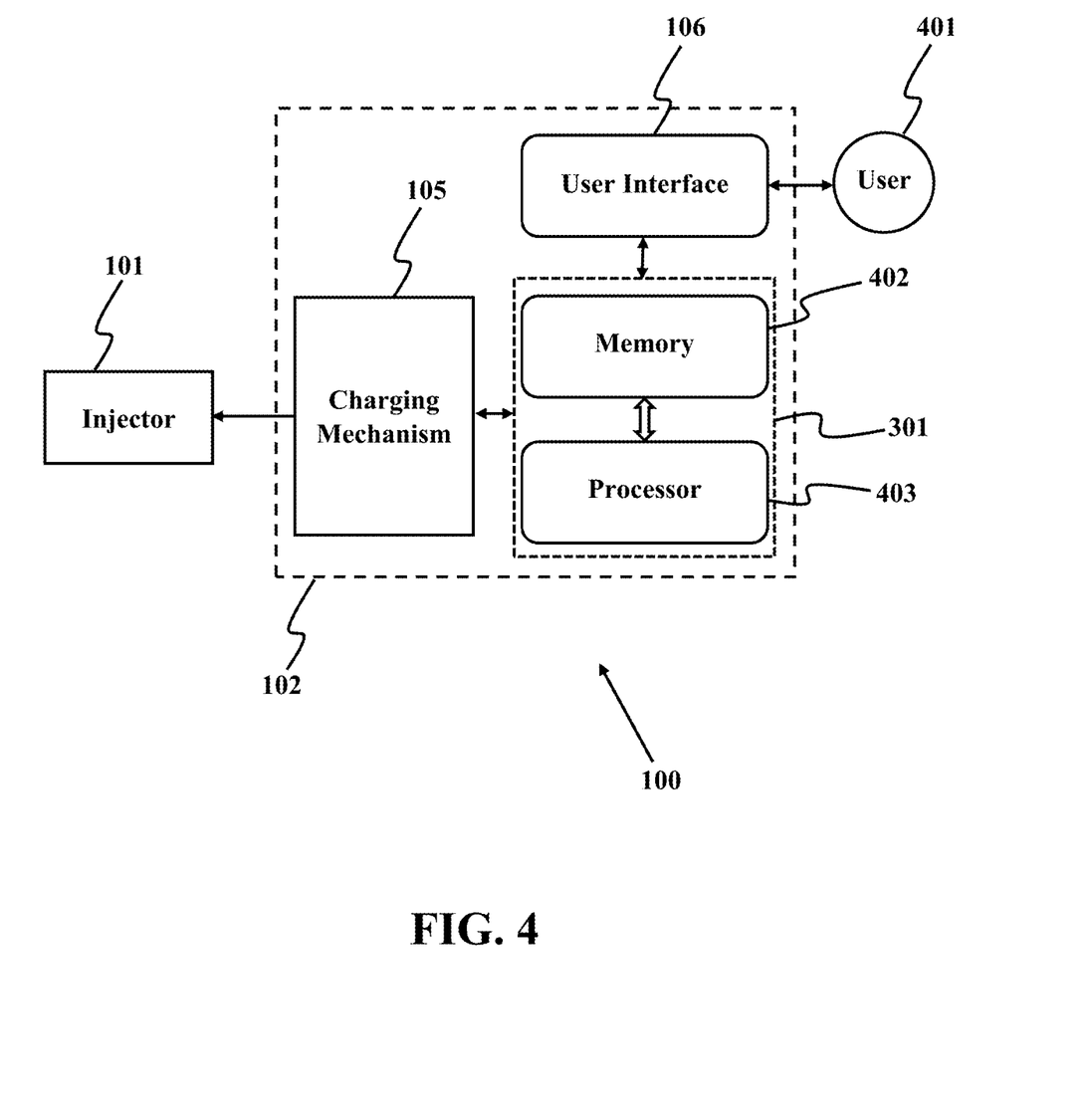
FIG. 4 is a simplified block diagram for a needle-free injection device, consistent with one or more exemplary embodiments of the present disclosure.

FIG. 4 is a simplified block diagram for needle-free injection device 100 of FIG. 1, consistent with one or more exemplary embodiments of the present disclosure. Referring to FIG. 4, controller 301 may further include a memory 402 and a processor 403. A user 401 may first attach a prefilled medication cartridge to needle-free injector 101. In an exemplary embodiment, referring to FIG. 2B, a prefilled cartridge such as cartridge assembly 218 may be screwed to threaded portion 202 of needle-free injector 101. User 401 may then place needle-free injector 101 in smart charging assembly 102 for charging needle-free injector 101 to a desirable extent.

With further reference to FIG. 4, in an exemplary embodiment, user 401 may select via user interface unit 106, a body type for a patient receiving the injection. The body type may be defined by different factors, such as body mass index, anatomical site of injection, age, and gender. The body mass index (BMI) may be calculated based on the weight and the height of the patient receiving the injection. For example, BMI may be defined as weight/height$^2$. According to an exemplary embodiment, user 401 may select the body type using a set of predefined options presented by user interface unit 106. The predefined options may include but are not limited to: child, average-weight adult with a BMI of 19-24, and heavy-weight adult with a BMI of 25-35. According to an exemplary embodiment, user 104 may enter parameters such as age, gender, height, and weight of the patient receiving the injection via user interface unit 106. User interface unit 106 may then transmit these parameters to controller 301 where the parameters may be stored on memory 402. In an embodiment, memory 402 may further include executable instructions to cause processor 403 to determine a body type for the patient based on the received parameters (e.g., BMI, anatomical site of injection, age, and gender).

According to an exemplary embodiment, controller 301 may be configured to determine an extent to which needle-free injector 101 must be charged. To this end, memory 402 may further include executable instructions to cause processor 403 to correlate the determined body type with a skin thickness; determine the amount of injection force required to successfully force a liquid medication into the subcutaneous tissue based on the skin thickness; calculate a distance by which the spring of needle-free injector 101 must be compressed in order to exert the determined amount of injection force on the liquid medication; and cause charging mechanism 105 to charge needle-free injector 101 according to the calculated distance.

The body type of the patient may be correlated with the skin thickness of the patient and the skin thickness of the patient may determine the required depth of penetration for the liquid medication. For example, for a child, the required depth of penetration may be about 4 mm, while for an average-weight adult, the required depth of penetration may be about 6 mm or in case of a heavy-weight adult, the required depth of penetration may be up to about 9 mm.

Referring to FIG. 4, needle-free injector 101 may be calibrated in order to determine the amount of injection force required to be exerted by needle-free injector 101 on the liquid medication to force the medication into the patient's body with the required depth of penetration. For example, for a needle-free injector with a spring that has a spring constant of about 6 N/mm, the required injection force may be calculated to be about 26 N for a child, about 36 N for an average-weight adult, and about 54 N for a heavy-weight adult. In a spring-loaded injector, this required amount of injection force may be converted by Hooke's law to the distance by which the spring must be compressed.

Referring to FIGS. 3 and 4, once the distance by which spring 207 must be compressed is determined, controller 301 may cause linear actuator 107 to move injector piston 103 against the injection force of spring 207 for the determined distance. For example, if the determined distance is 9 millimeters for a patient, controller 301 may cause linear actuator 107 to move injector piston 103 against the injection force of spring 207 for 9 millimeters. Referring to FIG. 2C ratchets 204 on injector piston 103 may be spaced apart by equal distances. It should be appreciated that the distance between two consecutive ratchets corresponds to an incremental injection force that may be applied by injector piston 103. According to some exemplary embodiments, the equal distances between ratchets 204 may be at least 2 mm. Once injector piston 103 is moved against the injection force of spring 207 for the determined distance, finger 217 may engage a ratchet on injector piston 103 and hold injector piston 103 at that predetermined distance. The user may then remove charged needle-free injector 101 from smart charging assembly 102. By placing needle-free injector 101 against a specific injection site on the patient's body and pressing trigger mechanism 104, injector piston 103 may be released in response to the injection force applied by compressed spring 207. The released injector piston 103 may then apply a force on cartridge piston 220 to shoot the liquid medication out of medication cartridge 218.

Referring to FIG. 4, according to an exemplary embodiment, controller 301 may further be configured to store the number of injections performed by needle-free injector 101, and the amount of liquid medication injected to a specific patient on memory 402. Memory 402 may further include executable instructions to cause processor 403 to display the number of injections performed by needle-free injector 101, and the amount of liquid medication injected to a specific patient on user interface unit 106. According to an embodiment, memory 402 may further include executable instructions to cause processor 403 to create an alarm via user interface unit 106 for the user 401 to replace spring 207 of needle-free injector 101.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. An adjustable needleless injection system for subcutaneous injection of a liquid medication to a patient, comprising:
   a medication cartridge configured to hold the liquid medication, the medication cartridge including a cartridge piston;
   a spring-actuated injector coupled with the medication cartridge and configured to selectively apply injection force to the cartridge piston, the spring-actuated injector including:
      a spring-loaded injector piston with ratchets formed in a symmetrical arrangement along a portion of the injector piston, the injector piston including an injector spring positioned to apply the injection force to the injector piston;
      a spring-loaded trigger engaged with the ratchets on the injector piston to hold the injector piston in place against the injection force applied by the injector spring, the trigger configured to selectively release the injector piston responsive to the trigger being pushed down, the injector piston configured to release to move responsive to the injection force applied by the injector spring, the injector piston configured to apply the injection force to the cartridge piston to force the liquid medication out of the medication cartridge; and
   a charging mechanism configured to charge the spring-actuated injector by applying a charging force to the injector piston to move the injector piston against the injection force of the injector spring by a predetermined distance, the charging mechanism including:
      a linear actuator configured to engage the injector piston, the linear actuator applying the charging force to the injector piston to move the injector piston against the injection force of the injector spring by the predetermined distance;
      a user interface unit configured to receive a body type from a user;
      a processor coupled with the charging mechanism; and
      a memory coupled to the user interface unit and the controller, the memory storing executable instructions to cause the processor to:
         receive the body type from the user interface unit;
         correlate the received body type with a required injection force;
         calculate the predetermined distance based on the required injection force; and
         cause the linear actuator to move the injector piston against the injection force of the injector spring by the predetermined distance.

2. The adjustable needleless injection system according to claim 1, wherein the ratchets on the injector piston are spaced apart by equal distances, each ratchet corresponding to an incremental injection force to be applied by the injector spring to the injector piston.

3. The adjustable needleless injection system according to claim 2, wherein the ratchets on the injector piston are spaced apart by at least 2 mm.

4. The adjustable needleless injection system according to claim 1, wherein the user interface unit configured to receive the body type from the user as parameters selected from the group consisting of body mass index, age, gender, and anatomical site of injection.

5. The adjustable needleless injection system according to claim 1, wherein the injector spring with a spring constant between 2 N/mm and 7 N/mm.

6. An adjustable needleless injection system for subcutaneous injection of a liquid medication to a patient, comprising:
   a medication cartridge configured to hold the liquid medication, the medication cartridge including a cartridge piston;
   a spring-actuated injector coupled with the medication cartridge and configured to selectively apply injection force to the cartridge piston, the spring-actuated injector including:
      a spring-loaded injector piston with ratchets formed in a symmetrical arrangement along a portion of the injector piston, the injector piston including an injector spring positioned to apply the injection force to the injector piston;
      a spring-loaded trigger engaged with the ratchets on the injector piston to hold the injector piston in place against the injection force applied by the injector spring, the trigger configured to selectively release the injector piston responsive to the trigger being pushed down, the injector piston configured to release to move responsive to the injection force applied by the injector spring,
   the injector piston configured to apply the injection force to the cartridge piston to force the liquid medication out of the medication cartridge; and
   a charging mechanism configured to charge the spring-actuated injector by applying a charging force to the injector piston to move the injector piston against the injection force of the injector spring by a predetermined distance.

7. The adjustable needleless injection system according to claim 6, wherein the charging mechanism includes a linear actuator engaging the injector piston, the linear actuator configured to apply charging force to the injector piston to move the injector piston against the injection force of the injector spring by the predetermined distance.

8. The adjustable needleless injection system according to claim 7, further comprising:

a user interface unit configured to receive a body type from a user;

a processor coupled with the charging mechanism; and a memory coupled to the user interface unit and the controller, the memory storing executable instructions to cause the processor to:

receive the body type from the user interface unit;

correlate the received body type with a required injection force;

calculate the predetermined distance based on the required injection force; and cause the linear actuator to move the injector piston against the injection force of the injector spring by the predetermined distance.

9. The adjustable needleless injection system according to claim 6, wherein the injector piston comprises:

a first portion in a form of a ratchet rod with ratchets formed along the first portion; and a second portion in a form of a rod that is separated from the first portion by an extended retainer; the injector spring positioned around the second portion against the extended retainer.

\* \* \* \* \*